United States Patent [19]

Criscuolo

[11] 4,373,517

[45] Feb. 15, 1983

[54] ORTHOPEDIC ARM AND SHOULDER BRACE

[75] Inventor: James M. Criscuolo, New York, N.Y.

[73] Assignee: Thomas E. Spath, Brooklyn, N.Y.

[21] Appl. No.: 177,477

[22] Filed: Aug. 12, 1980

[51] Int. Cl.³ .............................................. A61B 17/18
[52] U.S. Cl. ...................................... 128/75; 128/77; 128/78
[58] Field of Search .................................. 128/68–69, 128/75–78, 84 R, 84 C, 85, 87, DIG. 23, 80 R, 80 A, 80 B, 80 F, 80 G

[56] References Cited

U.S. PATENT DOCUMENTS

| | | | |
|---|---|---|---|
| 3,029,810 | 4/1962 | Martin | 128/78 |
| 3,548,817 | 12/1970 | Mittasch | 128/78 |
| 4,180,870 | 1/1980 | Radulovic | 128/77 |

FOREIGN PATENT DOCUMENTS 277176  1/1970  U.S.S.R. ................................. 128/85

OTHER PUBLICATIONS

Zimmer Airplane Splint, Zimer Product Encyclopaedia, copyright 1980.
Mobile Arm Support, Prosthetics and Orthotics, International, 1980, 4, 101–105, ©Aug. 1980.

*Primary Examiner*—Richard J. Apley
*Assistant Examiner*—Carl Moy
*Attorney, Agent, or Firm*—Davis, Hoxie, Faithfull & Hapgood

[57] ABSTRACT

This invention comprises a reversible orthopedic brace for the human arm and shoulder, useful for supporting and immobilizing either arm for indefinite periods of time. The brace is simply constructed with improved adjustment and locking means so that it may be adapted for use with either arm. It comprises two or more interconnected harness members to be fastened about the wearer's torso, and which are maintained in parallel relationship and securely joined to form a unitary structure by a hip support assembly, a locking bar assembly and a main support assembly, the latter two assemblies cooperating to receive and adjustably secure an arm support assembly. All elements cooperate to distribute uniformly the weight of the wearer's immobilized arm to the shoulders and torso.

7 Claims, 10 Drawing Figures

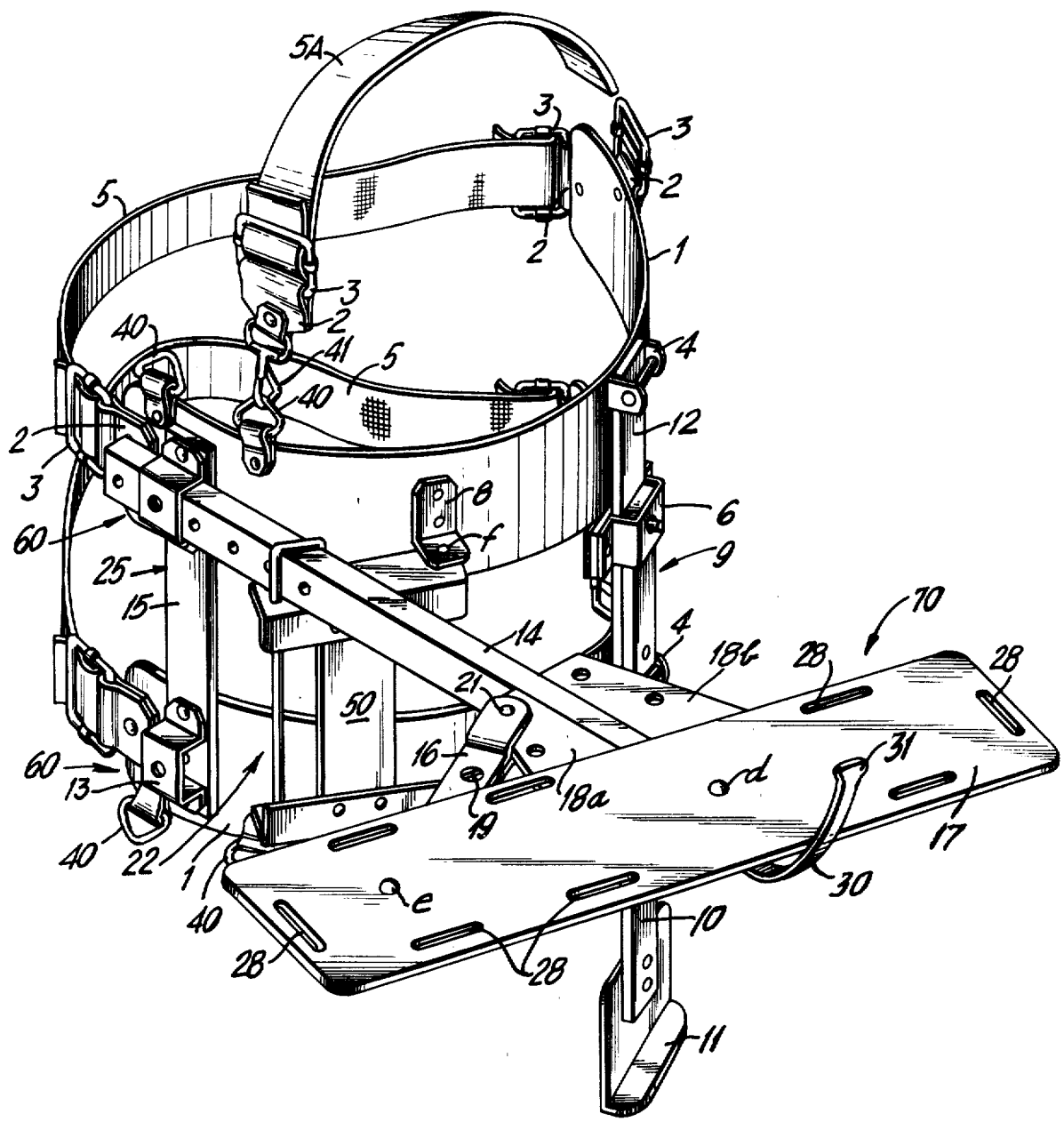
FIG.IA

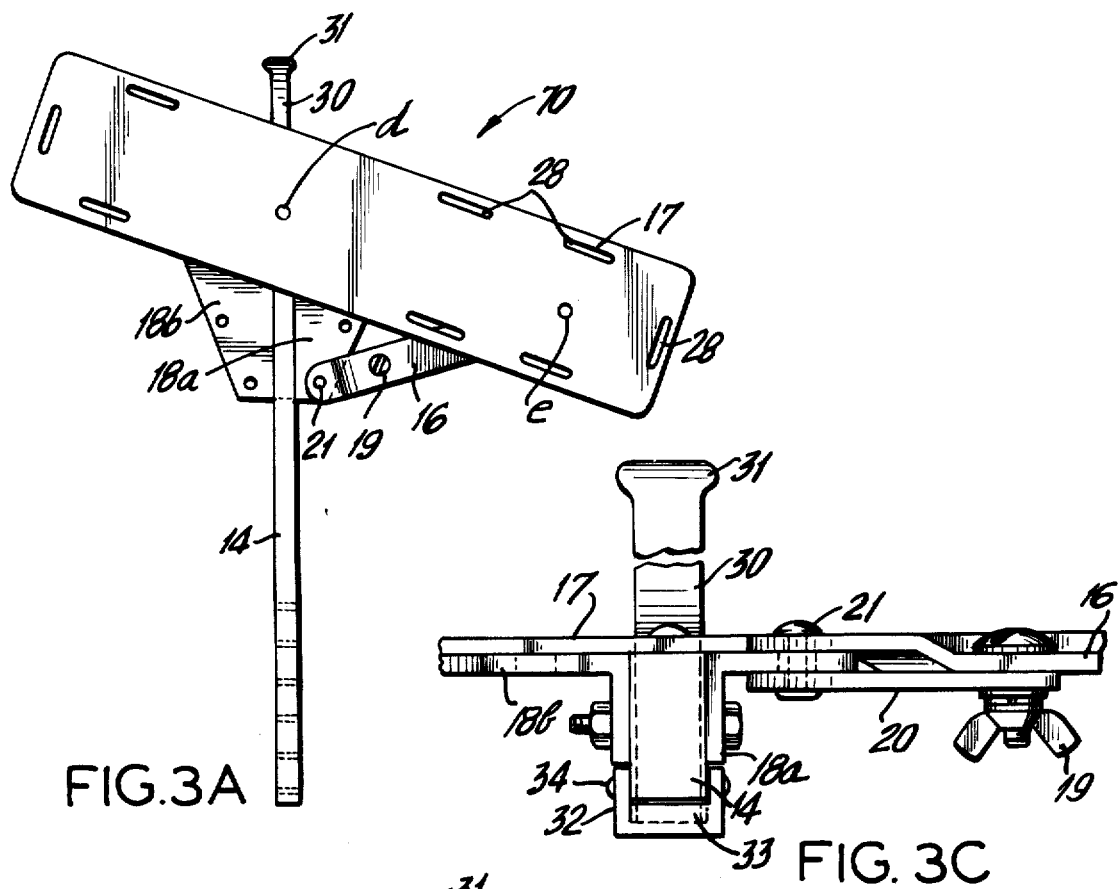
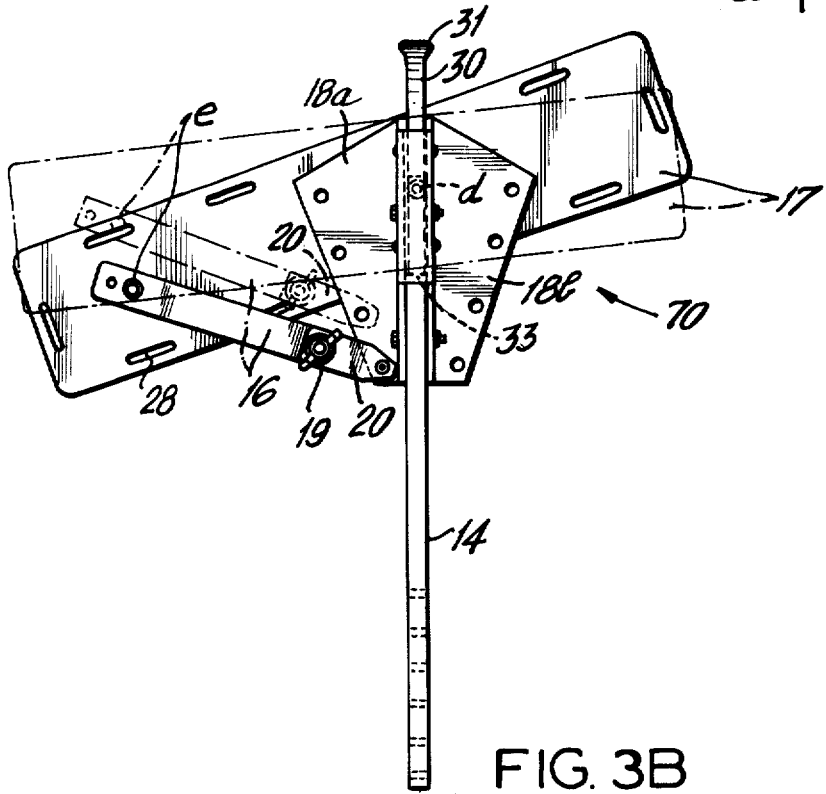

ORTHOPEDIC ARM AND SHOULDER BRACE

This invention relates to a reversible orthopedic brace for the human arm and shoulder which may be used to support and maintain the arm in a fixed position for an indefinite period of time. The brace is constructed in such manner that by making simple adjustments, it can be used with either the left or the right arm. The brace can be characterized as comprising a harness having means for fastening about the human torso, with two generally parallel rigid bands joined to one another by at least three assemblies, two of which assemblies cooperate to receive and secure an arm support assembly. It is described more fully below.

Often, total immobility of an arm must be maintained over a period of several weeks to allow an injury to heal. Prior art orthopedic arm and shoulder braces include plaster body casts which fully encompass the entire torso, including the shoulder and arm. Body casts can cause severe discomfort, body sores and, frequently, even pain, due to the weight of the cast and the total immobility imposed.

The prior art also includes non-reversible orthopedic braces of the harness type, in which the entire arm rests in a flexible metallic trough which is U-shaped in cross-section. The trough is connected to the harness and is supported by a bar extending from the trough to the lower portion of the harness structure. This type of brace also can cause pain and discomfort and may cause injuries to the arm which it supports. The brace has a tendency to shift position with respect to the arm, especially while the person wearing the device is reclining or asleep, and the arm can end up on the edge of the trough, a very uncomfortable resting place. Furthermore, the support bar of this prior art device concentrates virtually all of the weight of the arm and arm support assembly on the single point of attachment of the bar to the harness. This makes the wearer of the device very uncomfortable since the point of attachment is usually in the area of the rib cage and upper part of the hip, thus applying excessive pressure thereto. Yet a further problem with this device is the fact that it is made for either only a right arm or a left arm, i.e., it is not reversible, and must be produced in at least four different sizes to accomodate the normal variations in child and adult proportions.

Also in the prior art is a reversible brace device in which two harness members having parallel rigid bands are joined by a vertical bar positioned approximately under the armpit of the arm to be supported. A hinged plate which supports the upper arm is attached to the upper end of this vertical bar and upper harness under the wearer's arm. An adjustable support consisting of threaded rods and a turnbuckle connect the outer end of the hinged plate to the vertical bar. A forearm supporting plate is attached to a slotted bar which is adjustably secured to an "L" shaped traction bar extending out from under the upper arm support plate. This prior art device is referred to as an "airplane splint" and is sold under the trademark "Zimmer". While this device has the advantages of providing horizontal adjustment at the axilla and vertical adjustment of the forearm from horizontal to vertical, it suffers from drawbacks of the previously described device with respect to the configuration and location of the supporting plates, the discomfort to the wearer in the reclining position and concentration of the load or weight-bearing support on the wearer's hip.

A further disadvantage of the prior art devices is the use of wing nuts at the crucial points of adjustment. These wing nuts are generally positioned beyond the reach of the wearer and have a tendency to loosen, thereby requiring constant re-adjustment of the brace with the assistance of another person.

It is an object of the invention to provide a more comfortable orthopedic human arm and shoulder brace than has existed before.

It is another object of the invention to provide an arm and shoulder brace which is reversible, i.e., one device which may be utilized for either arm.

It is also an object of this invention to provide a single brace which can be adjusted to fit most adults and children.

It is still another object of the invention to distribute the force or load exerted by the weight of the arm and arm support assembly throughout the harness by means of a unitary structure.

It is a further object of the invention to provide a flexible-backed pin locking device which permits rapid and positive adjustment of the brace components to the desired configuration to meet the particular requirements of the individual wearer.

It is yet a further object of the invention to provide as simple a construction of the brace as possible.

The above and further objects and novel features of the invention will more fully appear from the following description when the same is read in connection with the accompanying drawings. It is to be expressly understood, however, that the drawings are for the purpose of illustration only, and are not intended as a definition of the limits of the invention.

In the drawings, wherein like reference characters refer to like parts throughout the several views:

FIG. 1A is a view of a preferred embodiment of the orthopedic arm and shoulder brace of the present invention, assembled for use with a left arm.

FIGS. 3A and 3B are, respectively, top and bottom views of an arm support assembly according to the invention.

FIG. 3C is a side view of a portion of the arm support assembly.

Figure 1B:
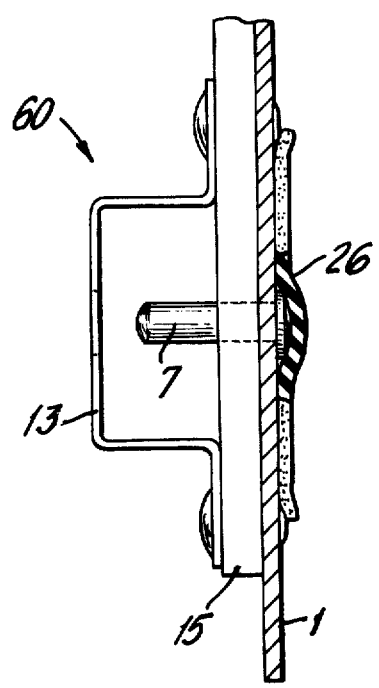
FIG. 1B is a vertical section of a stationary flexible-backed pin locking device according to the invention.
Figure 1C:
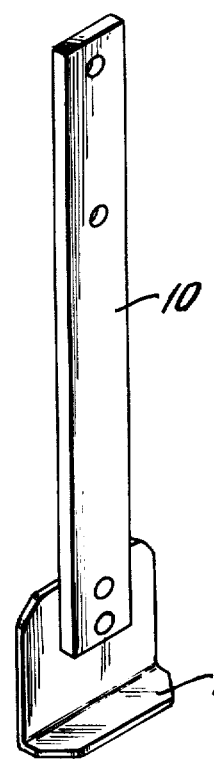
FIG. 1C is a view of a hip bar according to the invention.

In the embodiment of the invention depicted in FIGS. 1 through 4, the main frame, or harness, is comprised of at least two members which are identical adjustable flat bands 1, each having three buckle holders 2 and buckles 3 affixed thereto. Bands 1 are fabricated from a material which can be shaped to comfortably, but snuggly, conform to the torso of the individual wearer, and still be capable of being reshaped to fit subsequent wearers. Suitable bands 1 may be made from aluminum sheet stock approximately 3 inches (7.6 cm.) wide by 18 inches (45.7 cm.) long by 1/16 inches (0.16 cm.) thick. A buckle holder 2 and a buckle 3 are affixed to each end of each band 1. The bands 1 are held snugly in place around the upper torso by fastening means, such as webs 5, adjustably secured by the buckles 3. Along the outer edges of upper and lower bands 1 are a buckle holder 2, a buckle 3 and a number of D-rings 40 affixed to each band to provide points of attachment for a shoulder strap 5A which is fitted snugly over either shoulder of the person wearing the brace. Strap 5A is fitted at one end with a snap hook 41 carried on an adjustable buckle 1 and buckle holder 2 for engaging the D-rings 40. The other end of strap 5A attaches to the buckle 3 which is along the outer edge of upper band 1. Snap hook 41 can be attached to any D-ring 40 on either band 1 to suit the comfort of the wearer. Strap 5A thus provides additional support for the brace by preventing it from slipping vertically down the torso of the wearer. The webs 5 and strap 5A may be made from any sturdy pliable material, such as cotton, canvas or nylon webbing, leather or similar material, which is capable of supporting the weight of the wearer's arm and the arm support assembly. Webs 5 can advantageously be provided with some degree of elasticity to provide additional comfort to the wearer.

Affixed perpendicularly to each band 1 in a vertical position are main support assembly 22, locking bar assembly 25 and hip support assembly 9. These are the load bearing and distributing elements. Assembly 9 is comprised of a rigid bar 12 which is fitted with at least two slot-forming members 4 at either end and which are attached to the outer edges of upper and lower bands 1. Members 4 are adapted to receive the ends of bar 12 thus allowing hip support bar 10 to be vertically adjusted with relation thereto. Bar 12 is securely attached to bands 1 at a position which is approximately one-quarter to one-third of the length of the bands, measured from the end which is at the back of the wearer. Slidably affixed to bar 12 is independent flexible-backed pin lock 6, which will be described in detail below. Bar 12 preferably has at least three bores at regularly spaced intervals along its vertical length between upper and lower bands 1. Hip support bar 10 is approximately 12 inches (30.5 cm.) long and preferably has at least two bores adjacent its upper end, the bores being disposed vertically along its length and approximately 1 inch (2.5 cm.) apart. Hip support bar 10 has an L-shaped plate 11 at its lower end. Plate 11 can be approximately 2 inches (5.1 cm.) long and 4 inches (10.2 cm.) wide. The functioning of this element of the invention will be described more fully below.

Locking bar assembly 25 is also rigidly attached to bands 1 and is comprised of bar 15 and pin locking devices 60. Bar 15 is rigid and is attached at its opposite ends adjacent the ends of upper and lower bands 1 corresponding to the chest position of the wearer. Affixed to the surface of bar 15 and proximate its ends are slot-forming members 13, which comprise a part of stationary flexible-backed pin locking device 60. Slot-forming members 13 each have a bore which is coaxially aligned with bores of similar diameter in bar 15 and bands 1. Attached to the backs of bands 1, in opposition to slot-forming members 13, is a thin slab of elastic material 26, which engages the head of free-moving pin 7. Elastic material 26 is cemented, riveted, or otherwise affixed at its periphery to bands 1. Free-moving pin 7 is sufficiently long and of the diameter required to pass through and extend beyond the bores of both bands 1 and bar 15.

Figure 2:
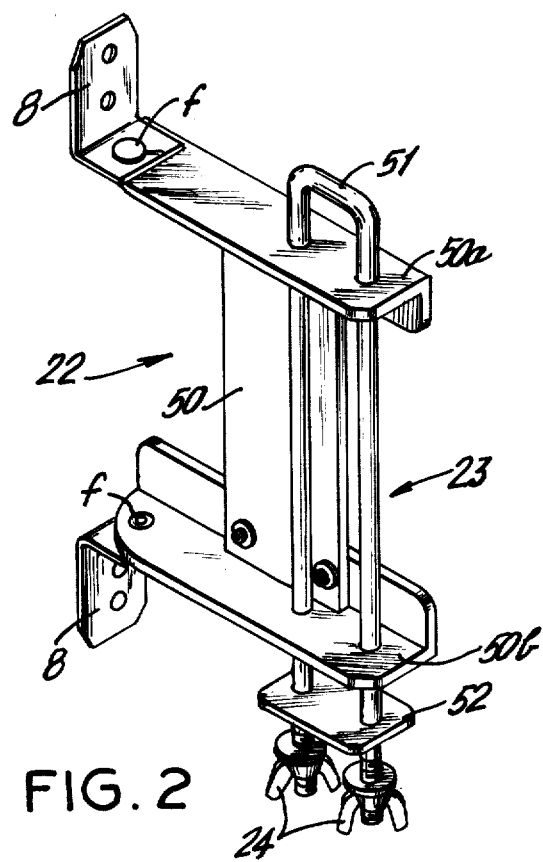
FIG. 2 is a pivotable main support and locking member for use in interconnecting the harness members of the brace and in supporting the arm support assembly.

Main support assembly 22 is securely affixed to upper and lower bands 1 at a position intermediate to bars 12 and 15. Preferably, support assembly 22 is attached by pivoting means 8 which permit it to move in an arc in the horizontal plane about, or adjacent to, its points of attachment to bands 1. This rotational movement can be accomplished by means of ball and socket joints, hinge plates, or as shown in FIG. 2, pin-type pivot points "f". Main support assembly 22 functions to adjustably fix the arm supporting assembly in relation to both the anterior and, in cooperation with the locking means on bar 15, the lateral positions of the torso of the wearer, and to receive and, in cooperation with bars 15 and 12, distribute the loading applied to the arm supporting assembly.

In the illustrative embodiment of FIG. 2, main support assembly 22 comprises a body element 50; upper and lower pivotal fastening means 8 for securing the body element 50 to the bands 1 while permitting the body element to rotate about pivot points "f" to define a horizontal arc; and support locking means 23, which cooperates with body member 50 to receive and secure a horizontal element of the arm supporting structure. Main support member 22 provides a means for adjustment to a variety of imposed leverage forces and permits the brace to be adapted to torsos of different sizes and shapes. Assembly 22 also performs the following important functions: (a) it locks the arm support bar 14; (b) it transmits the stress; (c) it provides leverage; and (d) it provides the means, through the pivoting or swivel action, for adjusting the brace to the most desirable and comfortable position for the individual wearer. In the illustrative embodiment of FIG. 2, support locking means 23 comprises a generally U-shaped rod 51 which passes easily through a pair of appropriately spaced holes in horizontal projections 50a and 50b of the body element 50, and thereby forms an aperature for receiving bar 14. Rod 51 terminates in threaded ends upon which wing nuts 24 are tightened against locking plate 52, or other conventional lockwashers, or the like. The dimensions of the U-shaped rod 51, or its functional equivalent, is determined by the configuration of the horizontal element of the arm supporting assembly, as will be appreciated from the description which appears below. Threaded U-shaped rod 51 and wing nuts 24 are preferred to provide for their easy loosening when the brace is to be inverted for use with the other arm.

As illustrated in FIGS. 3A, 3B and 3C the arm support assembly 70 comprises horizontal support bar 14, forearm plate 17, lock bar 16, lock bar peg 21, short lock bar assistant 20, wing nut and bolt assembly 19, and angle pieces 18a and 18b. The arm support bar 14 has a series of bores at one end thereof and angle pieces 18a and 18b permanently affixed to the other end. Rotatably affixed to arm support bar 14 at point "d" is forearm plate 17 which provides a surface to which the forearm of the wearer is securely immobilized. One end of lock bar 16 is rotatably affixed to the forearm plate 17 at point "e". The other end of lock bar 16 and one end of short lock bar assistant 20 engage angle piece 18a and are secured to it by lock bar peg 21, which is permanently affixed to lock bar 16 but which fits through the bore provided in short lock bar assistant 20. Wing nut and bolt assembly 19 is used to secure the other end of short lock bar assistant 20 to lock bar 16. It will also be understood that providing additional bores along the length of the horizontal surfaces of angle pieces 18a and 18b will permit wide latitude in the adjustment of the angle which forearm plate 17 forms with respect to support bar 14. This, in turn, determines the angle which the forearm forms with respect to the upper arm.

A plurality of slots 28 are provided about the periphery of plate 17 through which can be passed strips of bandage or other material used to secure the wearer's forearm to the plate. In an alternative manner of use, the wearer's arm can be suspended under the plate 17 in a fabric sling. In that case, the sling straps, conventionally made of wide candle wicking, will be passed up and/or appropriately laced through, slots 28 to secure the sling.

As illustrated in FIGS. 3B and 3C the arm support assembly can also be fitted with traction bar 30 which is inserted in the chamber created by affixing U-shaped channel 32 to the underside of support bar 14. Traction bar 30 is generally L-shaped, with the leg projecting above plate 17 terminating in projections 31 that are designed to facilitate the retention of an elastic bandage or other traction producing means. Channel 32 is securely affixed to bar 14 by fastening means 34, which can be screws or rivets. Channel 32 terminates at closed end 33. When it is desired to maintain the wearer's arm in traction, the traction bar 30 is inserted in channel 32 to contact end piece 33; an elastic bandage is then wrapped about the wearer's upper arm and/or forearm and the upwardly projecting leg of bar 30 and then secured to provide the desired tractive force. The forearm is then immobilized on plate 17 as previously described. The tension on the traction means extending between the upper leg of bar 30 and the wearer's arm maintains the bar in the fixed position in channel 32.

As illustrated, the assembly 70 is adapted to receive the left arm of the wearer. In order to reverse the arm support plate 17 for use with the right arm, wing nut and bolt assembly 19, short lock bar assistant 20, and lock bar peg 21 are disassembled. Forearm plate 17 is then rotated about point "d" and the previously mentioned elements are reassembled using a bore in the other angle piece 18b attached to arm support bar 14.

As an alternative to the above described mode of adjusting the angle which forearm plate 17 forms with respect to arm support bar 14, it will be readily understood that an arcuate adjustable lock bar can be used in place of lock bar 16 and short lock bar assistant 20, which are shown in FIGS. 3A, 3B and 3C.

The arm support bar 14 and forearm plate 17 can be constructed of any rigid material, such as wood, metal or plastic for example, which is capable of withstanding the load of the arm being supported. An appropriate length for the arm support bar 14 is approximately 18 inches (45.7 cm.). The dimensions of the forearm plate 17 may be approximately 4 inches (10.2 cm.) wide and 18 inches (45.7 cm.) long. These dimensions will accommodate the great majority of adult and adolescent wearers. Dimensions of braces used for children and others of unusual proportions can be adjusted according to the specific need of the wearer.

The adjustment, use and functioning of the brace is facilitated by incorporation of the flexible-backed pin locking devices briefly described above with reference to elements 6 and 60. As shown in FIGS. 4B and 4C, the independent locking device 6 which is adapted to adjustably secure hip support bar 10 to bar 12 is constructed from a U-shaped slot-forming member 13, a back plate 45 and a sheet of flexible resilient material 26A. Elements 13 and 45 have axially aligned central bore holes which are designed to allow free passage of the shaft of pin 7, but to engage and prevent passage of the flat head of pin 7. In this embodiment the entire assembly is secured by a pair of rivets 46. Also as shown in FIG. 4B, the shaft of pin 7 extends through the bore of member 13 a sufficient distance to permit the user to depress the pin shaft, by hand or otherwise, so that the flat head of the pin can be gripped by the fingers through resilient backing material 26A and pulled outwardly to disengage the shaft, for example, from the corresponding bore in the bar 10 and/or 12.

In this manner the hip support bar 10 can be adjusted for use by arm brace wearers of different heights and provide support to most. A longer bar 10 with attached plate 11 can be kept on hand to accommodate unusually tall wearers. Elastic material 26A should be sufficiently resilient to cause free-moving pin 7 to slide into engaging position in the bores of hip support bar 10 and bar 12 when the head of pin 7 is released. Since the back of the pin locking device is flat, and covered with a resilient material, it will not cause discomfort to the wearer.

Figure 4A:
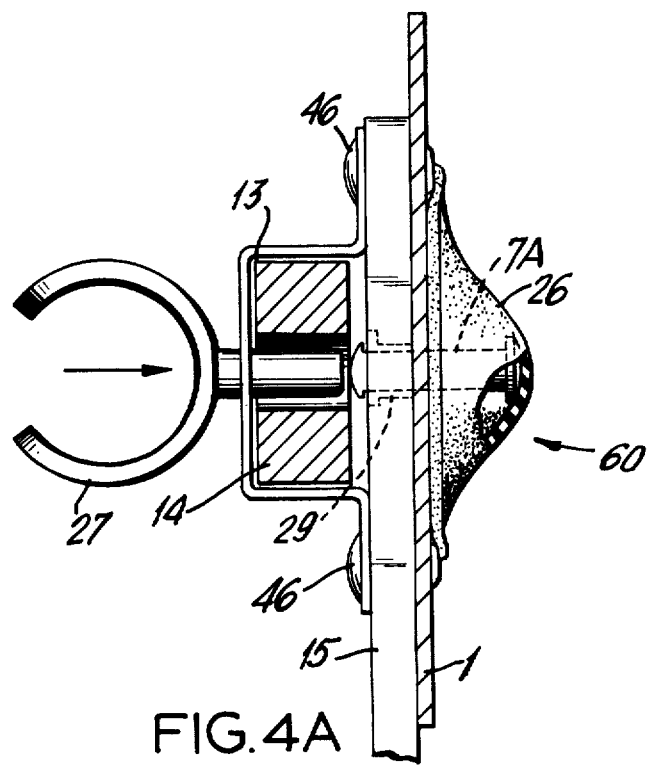
FIGS. 4A, 4B and 4C are a series of views of the flexible-backed pin locking devices used in the invention.
Figure 4B:
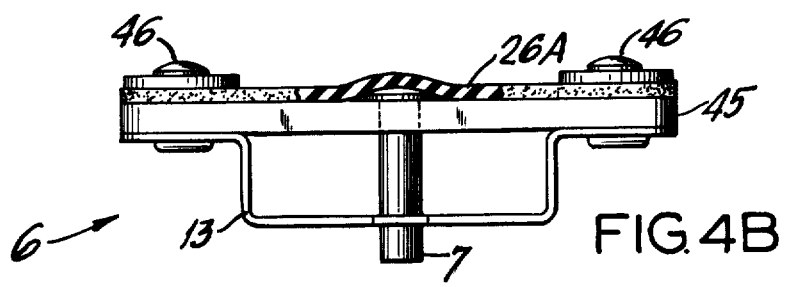
Figure 4C:
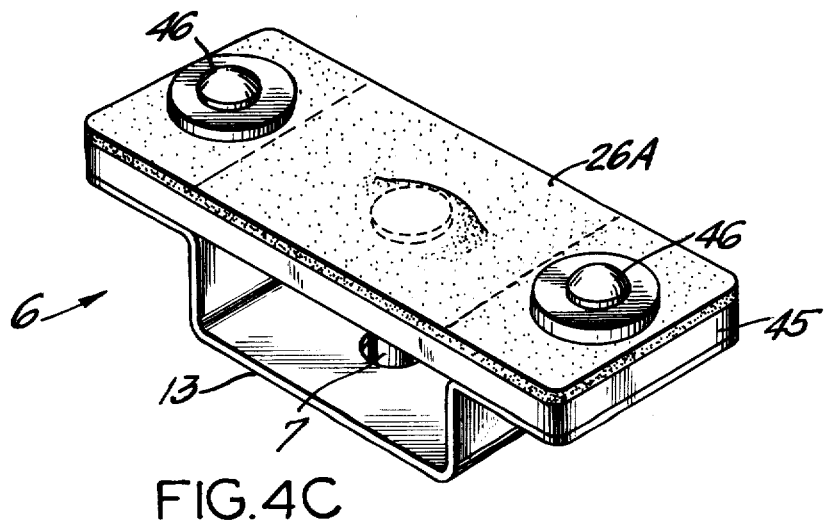

As shown in FIG. 4A, the stationary locking device 60 is likewise adapted to receive and adjustably secure a bar of rectangular cross-section by means of a flat-headed pin 7A and slot-forming member 13 with an axially aligned bore. In this embodiment the pin locking device is formed as an integral part of the stationary assembly of bar 15 and band 1, and secured together, as by rivets. Pin 7A can be fabricated by suitably modifying a rivet. In this instance the end of the shaft of pin 7A has been mushroomed slightly to prevent it from passing through the hole 29 in bar 15. The hole 29 in the bar which it is intended to engage and secure must be adapted, as by counter-sinking, to receive this mushroomed end of the shaft of pin 7A. The outer edges, or periphery, of resilient backing material 26 have been cemented by a suitable adhesive to the area around the flat head of pin 7A. As shown in FIG. 4A, the shaft of pin 7A does not project through member 13 and it is necessary to employ key 27, or similar means, to depress the shaft in order to disengage the bar 14. Here again, the resilient material 26 permits the user to grab the flat head end of the pin and pull it outwardly while the bar is adjusted or removed.

As contemplated by the present invention, arm support bar 14 rests atop surface 50a of support assembly 22, and is positioned between the shafts of U-shaped bolt 23, thus cooperating with slot-forming member 13 to rigidly secure the arm support assembly to the body harness.

Main support assembly 22 is designed and positioned to utilize the principle of the lever and acts as a fulcrum to distribute the load exerted by the arm and arm support assembly throughout the brace, thereby easing the discomfort of the wearer of the brace. This is a definite and significant advantage of my invention over the prior art devices described above.

As described above, in the majority of instances the forearm will be secured to plate 17, usually with some form of cushioning or padding between the arm and the plate. Should it become necessary to raise the entire forearm to a horizontal position higher than that permitted by the configuration of the brace as it is fitted to the wearer's torso, plate 17 can be fitted with a slab of foamed polystyrene, or other suitable material of appropriate thickness. This additional lightweight slab can be taped or secured to plate 17 by means of adhesive.

In the event that the forearm must be supported in an elevated position, i.e., the hand and wrist higher than the elbow, a wedge-shaped support of a lightweight material, such as expanded polystyrene foam or rigid polyurethane foam can be affixed to plate 17, after which the wearer's arm is secured as described above.

Alternatively, an adjustable plate, consisting of two hinged, rigid sections, one of which can be locked in an angle acute to the horizontal, can be substituted for plate 17, and mounted on horizontal support bar 14.

Another significant feature of the present invention is the relative freedom provided to the upper arm. The present brace is designed to allow the upper arm, i.e., the arm between the arm pit and the elbow, to be free, and it requires only that the forearm, i.e., the arm between the elbow and the fingers, rest in a fixed position on the forearm plate 17. The forearm may be kept immobilized by any convenient and practical fastening means, such as bandages or straps, by wrapping them around the entire arm support plate 17 after the forearm has been appropriately padded and positioned thereon, or by using the slots 28, as described above. The upper part of the arm can be secured in a splint when necessary and secured to the brace.

In order to provide additional support to the wearer of the brace, the upper arm may be placed in a comfortable fabric sling, the ends of which are then wrapped or otherwise secured to the arm support bar 14. When properly applied to the upper arm, such a sling will relieve the strain on the wearer's arm when the wearer has assumed a reclining position. This aspect of the invention is particularly useful when the wearer is attempting to sleep or rest. Ace bandages, standard fabric slings or like materials, having fastening means such as straps or hooks are suitable for this purpose.

Another significant advantage is provided by the hip support bar 10 and L-shaped plate 11 of my invention. The plate 11 should rest comfortably on the human hip or buttock when the wearer of the brace is standing or moving about. The hip bar and plate provide additional support for the arm and arm support assembly which is transmitted to upper and lower bands 1 at their points of attachment and further distribute the forces exerted. Moreover, when the wearer is seated, the hip support bar 10 when properly adjusted in the manner described above, also permits the horizontally projecting leg of plate 11 to rest on the seat. This feature significantly enhances the comfort to the wearer of the brace by eliminating, or greatly reducing, the load which he must bear.

A further advantage of the brace of the present invention is the simplicity and ease with which the elements may be adjusted, requiring virtually no tools. The wing nuts can usually be adjusted by hand and free-moving pins 7 or 7A may be depressed quite simply using either the finger or the key 27, as already has been described.

A still further advantage of the present invention is the inability of the locking means to disengage accidentally. Free-moving pins 7 or 7A are disengaged by depressing them back toward the wearer of the brace, thus making accidental disengagement improbable.

A still further advantage of the present invention is its reversible character. As shown in FIG. 1A, the brace is assembled for use with a left arm. In order to use the brace with a right arm, it is necessary only to disconnect the arm support assembly 70 and the hip support bar 10 from the harness members, disengage shoulder strap 5A from the D-ring and bucklet to which it is attached, reverse forearm plate 17 as described above, turn the harness upside down, reinsert the arm support assembly 70 and hip support bar 10 into the corresponding fittings and re-attach shoulder strap 5A.

For additional comfort to the wearer, all elements of the invention which are meant to come into contact with a part of the wearer's body may be padded with a material such as flexible resilient polyurethane foam, sheepskin or other soft material.

Unless otherwise specified, all of the elements described above can be fabricated from aluminum. It has favorable weight-to-strength ratios; can be easily machined, cut and worked; presents no allergy problems, and is extremely resistant to rust and corrosion under most conditions. Many of the elements can be further reduced in weight and aesthetically improved in appearance if cast, molded or machined from polymeric materials readily available to the art.

A wide variety of locking, fastening and adjustment means can be employed in combination with, or in substitution for, those specifically described above without departing from the teachings and scope of my invention.

What is claimed is:

1. In a reversible orthopedic brace device for use on a human being to immobilize and support the arm and shoulder of the wearer consisting of a pair of upper and lower adjustable, generally parallel rigid bands terminating at positions approximating the chest and back of the wearer, and fastening means associated with the bands for mounting laterally the bands on the human torso, the improvement which comprises:
    (a) at least three vertically mounted rigid assemblies, the upper and lower ends of which are secured to the upper and lower rigid bands to thereby join the bands in a unitary structure;
    (b) a generally horizontal arm support assembly terminating at one end in a pivotally mounted, adjustable horizontal plate adapted to receive and support the forearm of the wearer; and
    (c) a vertical hip support bar terminating in a flat L-shaped plate; wherein at least two of the vertically mounted rigid assemblies cooperate to receive and adjustably secure the horizontal arm support assembly, and a third vertically mounted rigid assembly is adapted to receive and adjustably secure the vertical hip support bar to position the L-shaped plate proximate to the hip of the wearer.

2. The reversible brace of claim 1 wherein:
    (a) one of the vertically mounted rigid assemblies comprises a locking bar assembly comprising a first rigid bar, two slot-forming members secured to the first rigid bar at positions over-lying and adjacent the end of upper and lower bands corresponding to the chest of the wearer, and locking devices associated with each slot-forming member;
    (b) a second of the vertically mounted rigid assemblies comprises the hip support assembly comprising a second rigid bar affixed at either end to upper and lower bands, slot-forming means located at each end of the second rigid bar, an adjustable locking device slidably mounted on the second rigid bar, and a hip support bar terminating in an L-shaped plate which plate is located at a position corresponding to the hip of the wearer, the hip support bar adapted to be received by the slot-forming member on the second rigid bar and secured in a vertically adjustable position by the locking device;
    (c) the third of the vertically mounted rigid assemblies comprises a main support assembly comprising a rigid body member which is secured at either end to the upper and lower bands by pivotal fastening means, at a position intermediate the locking bar assembly and hip support assembly, and generally U-shaped locking means associated, and forming an aperture, with the rigid body member; and (d) the arm support assembly comprises a horizontal support bar, a generally flat forearm plate pivotally secured to one end of the bar to permit rotation in the plane of the plate, and adjustable locking means associated with the support bar and forearm plate; and wherein the end of the horizontal support bar of the arm support assembly is adapted to first pass through the aperture formed by the U-shaped locking means and rigid body member of the main support assembly, and then through the slot-forming member of the locking bar assembly and into contact with the associated locking device.

3. The brace of claim 2 wherein the U-shaped locking means associated with the body member of the main support assembly is on the opposite side of the body member and spaced apart from the pivotal fastening means to thereby permit adjustment of the arm support assembly with respect to the torso.

4. The brace of claim 2 wherein the locking devices associated with the locking bar assembly comprise a retractable locking pin which cooperates with the slot-forming member, and the end of the horizontal support bar of the arm support assembly is provided with a plurality of laterally spaced holes adapted to receive the locking pin, to thereby permit lateral adjustment of the position of the forearm support plate.

5. The reversible brace of claim 2 in which fastening means includes a shoulder strap, wherein both upper and lower bands are fitted with at least three spaced apart loop devices proximate their uppermost and lowermost edges, respectively, to provide points of attachment for the shoulder strap when worn over either shoulder of the wearer.

6. The brace of claim 2 which includes an L-shaped traction bar, one end of which traction bar projects vertically above and adjacent to the forearm plate, and the other end of which is slidably received in a closed-ended channel comprised of the horizontal support bar of the arm support assembly.

7. The brace of claim 2 in which the locking devices of assemblies (a) and (b) comprise retractable, flat headed locking pins retained in position by a resilient backing material.

* * * * *